(12) United States Patent
Nakazawa

(10) Patent No.: US 8,492,350 B2
(45) Date of Patent: Jul. 23, 2013

(54) THERAPEUTIC AGENT FOR PAIN DISEASE

(75) Inventor: Yoshitaka Nakazawa, Hyogo (JP)

(73) Assignee: Nippon Zoki Pharmaceutical Co., Ltd., Osaka (JP)

( * ) Notice: Subject to any disclaimer, the term of this patent is extended or adjusted under 35 U.S.C. 154(b) by 445 days.

(21) Appl. No.: 12/449,152

(22) PCT Filed: Feb. 6, 2008

(86) PCT No.: PCT/JP2008/051920
§ 371 (c)(1),
(2), (4) Date: Oct. 14, 2009

(87) PCT Pub. No.: WO2008/096775
PCT Pub. Date: Aug. 14, 2008

(65) Prior Publication Data
US 2010/0121040 A1 May 13, 2010

(30) Foreign Application Priority Data
Feb. 8, 2007 (JP) ................... 2007-028721

(51) Int. Cl.
A61K 31/70 (2006.01)
C07H 5/04 (2006.01)
C07H 5/06 (2006.01)
C08B 37/00 (2006.01)
A01N 43/04 (2006.01)

(52) U.S. Cl.
USPC .......................................... 514/25; 536/18.7

(58) Field of Classification Search
None
See application file for complete search history.

(56) References Cited

U.S. PATENT DOCUMENTS

| 4,476,119 A | * | 10/1984 | della Valle et al. | ............. 514/25 |
| 5,045,532 A | | 9/1991 | della Valle et al. | |
| 5,438,125 A | | 8/1995 | Okamoto et al. | |

FOREIGN PATENT DOCUMENTS

| CN | 1762486 A | 4/2006 |
| CN | 1813797 A | 8/2006 |
| JP | A-52-34912 | 3/1977 |
| JP | A-62-145015 | 6/1987 |
| JP | A-1-157995 | 6/1989 |
| JP | A-1-163125 | 6/1989 |
| JP | A-5-105694 | 4/1993 |
| JP | A-9-301874 | 11/1997 |

OTHER PUBLICATIONS

Handa et al., "GD3 Synthase Gene Knockout Mice Exhibit Thermal Hyperalgesia and Mechanical Allodynia but Decreased Response to Formalin-Induced Prolonged Noxious Stimulation," Pain, 117(3), 271-279 (2005).*
Kakinoki et al., "Orally Active Neurotropin-Enhancing Agent Protects Against Dysfunctions of the Peripheral Nerves in Hyperglycemic Animals," Diabetes, 55(3), 616-621 (Mar. 2006).*
Venes et al.(eds.), Taber's Cyclopedic Medical Dictionary, 19th Edition, F. A. Davis Co., Philadelphia, PA, 2001, see pp. 1092-1094 ("Inflammation").*
Kim et al., "An Experimental Model for Peripheral Neuropathy Produced by Segmented Spinal Nerve Ligation in the Rat," Pain, 50, 355-363 (1992).*
Jensen et al., "A Clinical Picture of Neuropathic Pain," European Journal of Pharmacology, 429, 1-11, (2001).*
Negus et al., "Preclinical Assessment of Candidate Analgesic Drugs: Recent Advances and Future Challenges," J. Pharmacology Experimental Therapeutics, 319(2), 507-514 (2006).*
Backonja, M., "Defining Neuropathic Pain," Anesthesia and Analgesia, 97, 785-790 (2003).*
Committee for Medicinal Products of Human Use, "Guideleines on Clinical Medicinal Products . . . for Neuropathic Pain (Draft)," European Medicines Agency, 10 pages, London, UK (Jan. 26, 2006).*
Oster et al.; "Cyclic variation of sialic acid content in saliva;" American Journal of Obstetrics and Gynecology; 1972; pp. 190-193; vol. 114; No. 2.
Carlson et al.; "Oral and Intraperitoneal Administration of N-Acetylneuraminic Acid: Effect on Rat Cerebral and Cerebellar N-Acetylneuraminic Acid;" Journal of Nutrition; 1986; pp. 881-886; vol. 116; No. 5.
Morgan et al.; "Effects of Administration of N-Acetylneuraminic Acid (NANA) on Brain NANA Content and Behavior;" Journal of Nutrition; 1980; pp. 416-424; vol. 110; No. 3.

* cited by examiner

Primary Examiner — Lawrence E Crane
(74) Attorney, Agent, or Firm — Oliff & Berridge, PLC

(57) ABSTRACT

A method for treating neuropathic pain by administering a pharmaceutical preparation containing N-acetylneuraminic acid or a pharmaceutically acceptable salt thereof to a person in need of treatment of neuropathic pain. Examples of neuropathic pain include trigeminal neuralgia, postherpetic neuralgia, strangulated neuropathy, complex regional pain syndrome (CRPS), diabetic neuropathy, neuropathy caused by trauma, phantom limb pain, central pain, and neuropathic pain caused by drug therapy or radiation therapy.

3 Claims, No Drawings

THERAPEUTIC AGENT FOR PAIN DISEASE

TECHNICAL FIELD

The present invention relates to an analgesic agent for non-inflammatory pain diseases containing sialic acid or a pharmaceutically acceptable salt thereof as an effective ingredient.

BACKGROUND ART

Sialic acid is a general name for acyl derivatives of neuraminic acid. Although many kinds of sialic acids are present in the natural world, N-acetylneuraminic acid is most abundant among them and then the rate of N-glycolylneuraminic acid follows. Sialic acid is widely distributed in living organisms as a constituent for glycoprotein, glycolipid, glycopeptide, etc. It exits particularly on the cell membrane surfaces of animals and microbes bearing important biological functions such as participation in specific recognition mechanism of cells. Sialic acid has been regarded as important both medically and pharmaceutically as a substance participating in cancer, inflammation, immune, viral infection, cell differentiation, hormone receptor, etc. and various studies have been carried out for sialic acid and derivatives thereof.

During the course of repeated studies for pharmacological actions of sialic acid, the present inventors have found that sialic acid has a specific analgesic action. "Pain" is broadly classified into inflammatory pain which is caused by the inflammation of tissues by damage, etc. followed by releasing the algesic substances and physiological pain (nociceptive pain) as well as neuropathic pain which is not accompanied by the inflammation as such. The neuropathic pain is a general name for the pain caused by damage and dysfunction of central nerve and peripheral nerve and also for the non-inflammatory pain such as neuropathy, etc. by drug therapy or radiation therapy. Neuropathic pain causes, in addition to spontaneous pain, the symptoms such as hyperalgesia where pain threshold to nociceptive pain lowers and sharp pain (allodynia) induced by tactile stimulation which usually does not induce the pain. Once the morbid state is completed, it turns chronically whereby the outcome is very intractable unlike the inflammatory pain. Examples of the neuropathic pain disease include trigeminal neuralgia, postherpetic neuralgia, strangulated neuropathy (thoracic outlet syndrome, carpal tunnel syndrome, spinal canal stenosis, etc.), complex regional pain syndrome (CRPS), diabetic neuropathy, neuropathy caused by trauma, phantom limb pain and central pain after spinal damage or cerebral apoplexy.

At present, nonsteroidal analgesics, nonopioid analgesics, narcotic analgesics, etc. have been used for inflammatory pain and the therapeutic methods are able to be said to be almost established. With regard to non-inflammatory pain such as neuropathic pain however, although clarification for pathogenic mechanism has been already carried out, effective therapeutic drugs are little and there have been demanded clarification of morbid state and established therapeutic method therefor. The present inventors have found that sialic acid shows an analgesic action to model animals in morbid state of non-inflammatory pain and achieved the present invention. Although it has been reported already that sialic acid exhibits an anti-inflammatory action (refer to Patent Documents 1 and 2), there has been neither disclosure nor suggestion at all for its analgesic action to non-inflammatory pain.

Patent Document 1: Japanese Patent Laid-Open Publication No. 62/145,015
Patent Document 2: Japanese Patent Laid-Open Publication No. 01/163,125

DISCLOSURE OF THE INVENTION

Problems that the Invention is to Solve

An object of the present invention is to provide an analgesic agent for non-inflammatory pain diseases containing sialic acid or a pharmaceutically acceptable salt thereof as an effective ingredient.

Means for Solving the Problems

The present inventors have found that, since sialic acid shows an analgesic action to model animals in morbid state of non-inflammatory pain, it is useful as an analgesic agent for non-inflammatory diseases such as neuropathic pain whereby the present invention has been achieved.

Advantages of the Invention

Sialic acid which is an effective ingredient of the drug of the present invention showed an analgesic action to model animals in morbid state of neuropathic pain which is a non-inflammatory pain. Accordingly, the analgesic agent of the present invention is useful as a drug for the treatment of non-inflammatory pain diseases such as neuropathic pain.

BEST MODE FOR CARRYING OUT THE INVENTION

The present invention relates to an analgesic agent to non-inflammatory pain diseases containing sialic acid or a pharmaceutically acceptable salt thereof as an effective ingredient.

Sialic acid which is an effective ingredient of the analgesic agent of the present invention include the pharmaceutically acceptable salts of thereof with alkali metal such as sodium or potassium, with alkaline-earth metal such as calcium, magnesium or barium, with other metal such as aluminium or zinc, with organic amine or with ammonium. These salts can be produced from sialic acid in a free form, or converted reversibly, in accordance with a known method. Existence of not less than 15 kinds of sialic acid has been known and many of them are N-acetyl or N-glycolyl substances and have N-acyl or O-acyl group. Any of them is able to be used in the present invention. Preferred examples thereof include N-acetylneuraminic acid which exists most abundantly in the natural world and is a representative sialic acid and a pharmaceutically acceptable salt thereof. Acute toxicity of N-acetylneuraminic acid is disclosed in Patent Document 1 and the toxicity is shown to be very low and safe. With regard to sodium N-acetylneuraminate, it is also shown to be very lowly toxic as a result of acute toxicity tests (refer to Example 8 of the Japanese Examined Patent Publication No. 63/028,411).

When the steric isomers such as cis-trans isomer, optical isomer and conformational isomer, or hydrate and metal complexes of the sialic acid of the present invention exist, the present invention includes any and all of them.

The sialic acid of the present invention can be made into pharmaceutical preparations by a combination with a suitable pharmaceutical carriers or diluents according to any conventional methods, for example, preparations for oral administrations (e.g. tablets, capsules, powders, liquids, etc.) and for parenteral administrations (e.g. for subcutaneous, intravenous, intramuscular, intrarectal and intranasal administrations). At preparing, the sialic acid of the present invention may also be used in the form of the pharmaceutically acceptable salt, and can be used either solely or jointly together with other pharmaceutically effective ingredients.

As to an orally administering preparation, the sialic acid per se or together with an appropriate additive such as an excipient, a binder, a disintegrating agent, a lubricant, a bulking agent, a moisturizer, a buffer, a preservative or a flavor is able to be made into tablets, diluted powder, granules or capsules. Furthermore, depending upon the type of the disease and patient, it is possible to prepare other preparations than those which were mentioned already, for example, suitable preparations for the therapy, such as injections, suppositories, inhalations, aerosols, syrups, collyriums, medicines for external use (e.g. ointments), etc.

The preferred dose of the analgesic agent of the present invention may vary depending upon the object to be administered the patient, form of the preparation, method for the administration, term for the administration, etc. and, in order to achieve a desired effect, 10-5000 mg per day, preferably 50-3000 mg per day may be usually given to common adults by oral route. In the case of a parenteral administration such as by injection, lower doses than the above given dose by oral route have an effect.

EXAMPLES

Test for Analgesic Effect

Test for analgesic effect was conducted using Chung model rats which are models of neuropathic pain. Male rats of Wistar strain of 9 weeks age were used as experimental animals and model rats were prepared according to a method of Kim and Chung (*Pain*, vol. 50, pages 355 to 363, 1992). Thus, when they were in 10 weeks age, rat L5 spinal nerve was exposed and the periphery side of L5 dorsal root ganglion was strongly ligated with 5-0 silk yarn under anesthetizing with pentobarbital (40 mg/kg, intraperitoneal administration) to conduct a nerve damage. The animals were placed in a transparent acrylic cage where the bottom was wire net, 50% reaction threshold values were calculated by an up-down method using a von Frey filament (manufactured by North Coast Medical Inc.) according to a method of Chaplan, et al. (*J. Neurosci. Method*, vol. 53, pages 55 to 63, 1994) and the effect of the test substance to allodynia was measured. Those which showed a stable decrease in threshold value of from 1 g to less than 4 g by the measurement of 50% reaction threshold values after the spinal nerve damage were used for the test. In those experimental animals, each group comprised seven animals using the 50% reaction threshold values after the nerve damage as an index and the group constitution was done in such a manner that mean values of a nerve damage control group and of a test substance-administered group were made nearly uniform.

N-acetylneuraminic acid as a test substance was intraperitoneally administered in a single dose (120 mg/kg). A 0.5% CMC-Na (w/v) solution/physiological saline was similarly administered to the nerve damage control group (control group). After 30 minutes from the administration of a test substance, pain tests were conducted and the calculated 50% reaction threshold values were expressed in terms of mean value±standard deviation for each group. An example of the results of the above test is shown in Table 1. Test for significant difference was conducted using Dunnett's multiple comparison method for a comparison in multiple groups between the nerve damage control group and the test substance-administered group and it was judged that $P<0.05$ is significantly different.

TABLE 1

| Groups | 50% Reaction Threshold Values (g) | |
|---|---|---|
| | Before Administration | After 30 minutes from Administration |
| Nerve Damage Control | 2.66 ± 0.25 | 2.84 ± 0.37 |
| N-Acetylneuraminic Acid | 2.63 ± 0.21 | 6.74 ± 1.64* |

*$P < 0.05$ (Dunnett's Multiple Comparison Test)

Further, in the same manner as the above test, N-acetylneuraminic acid as a test substance was orally administered in a single dose (300 mg/kg). Injection solvent was administered to a nerve damage control group (control group) in the same manner. After 60 minutes from the administration of a test substance, pain tests were conducted and the 50% reaction threshold values were calculated. Numbers of the animals were eight for each of the nerve damage control group and the test substance-administered group. An example of the above test result is shown in Table 2.

TABLE 2

| Groups | 50% Reaction Threshold Values (g) | |
|---|---|---|
| | Before Administration | After 60 minutes from Administration |
| Nerve Damage Control | 2.76 ± 0.20 | 2.96 ± 0.36 |
| N-Acetylneuraminic Acid | 2.75 ± 0.15 | 4.81 ± 0.35* |

*$P < 0.05$ (Dunnett's Multiple Comparison Test)

As a result of conducting the above analgesic effect tests, there was no big change in the 50% reaction threshold values before and after administration of the CMC-Na solution/physiological saline or the injection solvent in the nerve damage control group (control group) in both of single intraperitoneal injection and single oral administration. On the contrary, the 50% reaction threshold value in the test substance (N-acetylneuraminic acid) administered group showed a significant rise as compared with the nerve damage control group whereby the anti-allodynia action of the present invention compound or, in other words, a significant anti-analgesic effect to neuropathic pain was noted.

INDUSTRIAL APPLICABILITY

As shown in the above analgesic effect test, sialic acid exhibited a significant analgesic effect to model animals in morbid state of neuropathic pain. Unlike the inflammatory pain caused by inflammation, the neuropathic pain is morbid pain without inflammation caused by dysfunction of peripheral or central nerve itself. Accordingly, the analgesic agent of the present invention is useful as a drug for the treatment of non-inflammatory pain diseases such as neuropathic pain disease, for example, trigeminal neuralgia, postherpetic neuralgia, strangulated neuropathy (thoracic outlet syndrome, carpal tunnel syndrome, spinal canal stenosis, etc.), complex regional pain syndrome (CRPS), diabetic neuropathy, neuropathy caused by trauma, phantom limb pain, central pain after spinal damage or cerebral apoplexy and neuropathic pain caused by drug therapy or radiation therapy.

The invention claimed is:

1. A method for treating neuropathic pain for which the administration of non-steroidal analgesics is not effective comprising administering a pharmaceutical preparation containing N-acetylneuraminic acid or a pharmaceutically acceptable salt thereof to a person in need of treatment of neuropathic pain for which the administration of non-steroidal analgesics is not effective.

2. The method according to claim 1, wherein the neuropathic pain for which the administration of non-steroidal analgesics is not effective is selected from the group consisting of trigeminal neuralgia, postherpetic neuralgia, strangulated neuropathy, complex regional pain syndrome (CRPS), diabetic neuropathy, neuropathy caused by trauma, phantom limb pain, central pain, and neuropathic pain caused by drug therapy or radiation therapy.

3. The method according to claim 1, wherein the pharmaceutical preparation is an oral agent.

* * * * *